US008361522B2

(12) United States Patent
Ulmann et al.

(10) Patent No.: US 8,361,522 B2
(45) Date of Patent: Jan. 29, 2013

(54) COSMETIC AND/OR PHARMACEUTICAL COMPOSITIONS AND THEIR APPLICATIONS

(75) Inventors: André Ulmann, Paris (FR); Jean-Frédéric Sturer, Paris (FR)

(73) Assignee: Legacy Healthcare Holding Ltd, Valleta Vlt (MT)

( * ) Notice: Subject to any disclaimer, the term of this patent is extended or adjusted under 35 U.S.C. 154(b) by 255 days.

(21) Appl. No.: 12/526,493

(22) PCT Filed: Feb. 8, 2008

(86) PCT No.: PCT/FR2008/000152
§ 371 (c)(1),
(2), (4) Date: Aug. 7, 2009

(87) PCT Pub. No.: WO2008/113912
PCT Pub. Date: Sep. 25, 2008

(65) Prior Publication Data
US 2010/0104671 A1    Apr. 29, 2010

(30) Foreign Application Priority Data
Feb. 13, 2007    (FR) ..................... 07 01011

(51) Int. Cl.
*A61K 36/8962*    (2006.01)
*A61K 36/752*    (2006.01)
*A61K 36/00*    (2006.01)
(52) U.S. Cl. .......... 424/754; 424/736; 424/725
(58) Field of Classification Search .......... None
See application file for complete search history.

(56) References Cited

U.S. PATENT DOCUMENTS

| 5,773,241 A * | 6/1998 | Ericsson ............ 435/41 |
| 2003/0077336 A1 | 4/2003 | Maffetone |
| 2004/0076614 A1* | 4/2004 | Schur ............ 424/93.4 |

FOREIGN PATENT DOCUMENTS

| CH | 682217 | 8/1993 |
| DE | 28 44 614 | 5/1980 |
| DE | 195 33 777 | 3/1997 |
| DE | 20 2004 012 348 | 10/2004 |
| DE | 10 2004 011 968 | 9/2005 |
| DE | 10 2005 010 142 | 11/2005 |
| FR | 2 706 771 | 12/1994 |
| FR | 2 877 219 | 5/2006 |
| FR | 2 877 576 | 5/2006 |
| JP | 2000-044439 | 2/2000 |
| JP | 2000-247830 | 9/2000 |
| JP | 2003-201229 | 7/2003 |
| JP | 2006-104098 | 4/2006 |
| JP | 2006-342120 | 12/2006 |
| WO | WO 2005/120452 | 12/2005 |

OTHER PUBLICATIONS

Tzia et al. (Extraction Optimization in Food Engineering, National Technical University of Athens, Copyright 2005).*

* cited by examiner

*Primary Examiner* — Christopher R. Tate
*Assistant Examiner* — Deborah A. Davis
(74) *Attorney, Agent, or Firm* — Harness, Dickey & Pierce, P.L.C.

(57) ABSTRACT

Compositions are disclosed containing, as active ingredients, an extract of *Allium* species, an extract of *Citrus* species and either an extract of *Paullinia* species and an extract of *Theobroma* species, or an extract of *Salix* species and zinc sulphate, and the method of preparation of these compositions, and cosmetic and/or pharmaceutical application of these compositions.

7 Claims, No Drawings

COSMETIC AND/OR PHARMACEUTICAL COMPOSITIONS AND THEIR APPLICATIONS

CROSS-REFERENCE TO RELATED APPLICATIONS

This application is a National Phase Entry of International Application No. PCT/FR2008/000152, filed on Feb. 8, 2008, which claims priority to French Patent Application No. 07 01 011, filed on Feb. 13, 2007, both of which are incorporated by reference herein.

BACKGROUND AND SUMMARY

The invention concerns new compositions and the use of these compositions in cosmetics and/or their application as medicines.

Some cosmetic and/or pharmaceutical compositions containing fresh onion, iodine salts, citric acid and lemon juice have been described in the literature. These compositions can be used especially in cosmetics to encourage the regrowth of hair or in therapeutical indications to promote angiogenesis, stimulate the synthesis of collagen and stimulate the proliferation and activation of mast cells, and indeed in the treatment of certain cancers. Among the literature references that may be cited, for example, are the French patent applications No. 2 875 403, 2 877 219, 2 877 224, 2 877 576 and 2 877 408 or the Swiss patent application No. 682 217 A. The applicant has studied new compositions which are suitable for use in cosmetics or human therapy and which show superior activity and high stability without the disadvantages of the compositions described in the literature.

The object of the invention is thus new compositions characterised by the fact that they contain: an extract of Mum species, an extract of *Citrus* species and
   either an extract of *Paullinia* species and an extract of *Theobroma* species
   or an extract of *Salix* species and zinc sulphate.

Among these compositions, those which are of more particular interest are compositions as defined above, characterised in that they contain: an aqueous-alcoholic extract of *Allium* species, an aqueous-alcoholic extract of *Citrus* species and
   either an aqueous-alcoholic extract (atomised or not) of *Paullinia* species and an aqueous-alcoholic extract (atomised or not) of *Theobroma* species,
   or an aqueous extract (atomised or not) of *Salix* species and zinc sulphate.

Among the compositions according to the invention, those which are of most particular interest are compositions as defined above, containing from 65% to 93% of an aqueous-alcoholic extract of *Allium* species, from 5% to 33% of an aqueous-alcoholic extract of *Citrus* species, from 0.25% to 2.5% of an aqueous-alcoholic extract (atomised or not) of *Paullinia* species and from 0.25% to 2.5% of an aqueous-alcoholic extract (atomised or not) of *Theobroma* species and especially those containing from 65% to 93% of an aqueous-alcoholic extract of *Allium cepa*, from 5% to 33% of an aqueous-alcoholic extract of *Citrus lemon*, from 0.25% to 2.5% of an aqueous-alcoholic extract (atomised or not) of *Paullinia* species and from 0.25% to 2.5% of an aqueous-alcoholic extract (atomised or not) of *Theobroma* species. The term extract of *Allium* species or aqueous-alcoholic extract of *Allium* species refers particularly to aqueous-alcoholic extracts and native extracts obtained from all species of the genus *Allium* (family Liliaceae) and especially *Allium cepa*. Extract of *Citrus* species or aqueous-alcoholic extract of *Citrus* species refers particularly to aqueous-alcoholic extracts and native extracts obtained from all species of the genus *Citrus* (family Rutaceae) and especially *Citrus lemon*. Extract (atomised or not) of *Paullinia* species or aqueous-alcoholic extract (atomised or not) of *Paullinia* species refers particularly to aqueous-alcoholic extracts and native extracts obtained from all species of the genus *Paullinia* (family Sapindaceae) and especially *Paullinia cupana*. Extract (atomised or not) of *Theobroma* species or aqueous-alcoholic extract (atomised or not) of *Theobroma* species refers particularly to aqueous-alcoholic extracts and native extracts obtained from all species of the genus *Theobroma* (family Malvaceae) and especially *Theobroma cacao*.

Among the compositions according to the invention, those which are also of most particular interest are compositions as defined above containing from 65% to 93% of an aqueous-alcoholic extract of *Allium* species, from 5% to 33% of an aqueous-alcoholic extract of *Citrus* species, from 0.25% to 2.5% of an aqueous extract (atomised or not) of *Salix* species and from 0.1% to 1% of zinc sulphate, and especially those containing from 65% to 93% of an aqueous-alcoholic extract of *Allium cepa*, from 5% to 33% of an aqueous-alcoholic extract of *Citrus lemon*, from 0.25% to 2.5% of an aqueous extract (atomised or not) of *Salix* species and from 0.1% to 1% zinc sulphate hexahydrate. Extract of *Salix* species or aqueous extract (atomised or not) of *Salix* species refers to aqueous extracts obtained from all species of the genus *Salix* (family Salicaceae), especially *Salix alba*. The zinc sulphate used in compositions according to the invention may be in the form of the anhydrous salt or a polyhydrated salt, especially the hexahydrate.

The most preferred compositions according to the invention are:
   those containing approximately 87% of an aqueous-alcoholic extract of *Allium cepa*, approximately 12% of an aqueous-alcoholic extract of *Citrus lemon*, approximately 0.5% of an aqueous-alcoholic extract (atomised or not) of *Paullinia cupana* and approximately 0.5% of an aqueous-alcoholic extract (atomised or not) of *Theobroma cacao*,
   as well as those containing approximately 87% of an aqueous-alcoholic extract of *Allium cepa*, approximately 12% of an aqueous-alcoholic extract of *Citrus lemon*, approximately 0.5% of an aqueous extract (atomised or not) of *Salix alba* and 0.2% zinc sulphate hexahydrate.

Another object of the invention is a method for the preparation of compositions such as those defined above, involving the preparation of a master solution containing the extracts of *Allium* species and *Citrus* species and then mixing this solution either with an extract of *Paullinia* species and an extract of *Theobroma* species, or with an extract of *Salix* species and zinc sulphate, to give the required composition.

According to the preferred conditions for carrying out this process, the method is characterised in that the master solution is prepared by picking, cleaning and milling the *Allium* and the *Citrus*, macerating for several hours in alcohol and filtering, then adjusting the alcoholic extract and mixing with the other ingredients. In using this method of preparation for the compositions according to this application, a recommended procedure is to prepare the master solution from the constituents, by picking, cleaning and milling the *Allium* and the *Citrus*, mixing with 96° alcohol, macerating in the cold for 48 hours, filtering the master solution through 0.22-micron filters to give a water-alcohol extract with a low content of particles and then adjusting the extract obtained to 30° alcohol. This master solution is then treated, by simple mixing, either with the extracts (atomised or not) of *Paullinia* species and *Theobroma* species, or with the extract (atomised or not) of *Salix* species plus the zinc sulphate.

Compositions such as those described above exhibit interesting properties which make them suitable for use in cosmetics. In cosmetic applications, these compositions may be used in particular for controlling and/or stabilising any conditions affecting the skin, the scalp or other external parts of the body, and especially for slowing down the loss of hair, stimulating its growth, increasing its density, eliminating dandruff, offsetting the signs of ageing of the scalp and treating any disorders of the nails. For topical application, these compositions may thus be applied directly to the skin or the scalp at the rate of one to three applications daily in the form of solutions or concentrated lotions, for example, with a concentration of 5 to 30%, preferably approximately 20%. For cosmetic applications, the compositions may also be administered as food supplements in the form of granules, flexible capsules or drinks; depending on the final form required, and instead of using the product in the form of an aqueous alcoholic solution, it may be better to use the product as a dry form obtained from the solution, for example by atomisation, freeze-drying, concentration or secondary extraction of the aqueous-alcoholic solution with super-critical $CO_2$.

Compositions such as those described above also show very interesting pharmacological properties. They may therefore be administered to humans or animals as medicines, especially as therapeutic or prophylactic medicines. In particular, these compositions may be used for treating dermatosis, and more particularly dermatosis due to various cutaneous bacterial and viral infections, ageing of the skin, bleaching and whitening of the skin, vitiligo, acrodermatitis, light-induced (actinic) ageing of the skin and various conditions related to sunrays (photodermatosis), acne of any origin (vulgaris, inflammatory or papulo pustule), acne rosacea, lupus erythematosus, sensitive skin, insect stings, oily or dry skin, seborrheic disorders, alopecia of any origin, hair loss, pityriasis capitis, pelada, sensitive scalp, greasy hair, psoriasis and parapsoriasis of the scalp, dyshidrosis, warts and corns, scabies, angular cheilitis and oedema, or any diseases capable of affecting the nails.

In therapy, these compositions also have an effect on microvascularisation and an effect on the cicatrisation of wounds, affections of any origin, burns, blotchiness, Behçet's disease, cutaneous porphyria, angiomas and malignant metastases. They may also be used in therapy for treating disorders of keratinisation, as well as keratotic lesions, hyperkeratoses including keratoderma, dyskeratosis, Darier's disease, parakeratosis, ichthyosis, eczema, neurodermatitis, erythroderma, lichenification, scaly dermatosis, prurigo, cheloids and pustulosis. Finally they may be used in therapy for treating circulatory and vasomotor disorders, especially the functional signs during haemorrhoidal pressure, thrombotic affections, symptoms associated with veno-lymphatic insufficiency, heavy legs and paresthesia.

The compositions may be administered as such or in mixtures with one or more other compounds in the form of pharmaceutical compositions containing an effective dose as the active ingredient, together with standard, pharmaceutically inert excipients and/or additives. These pharmaceutical compositions may be administered by the buccal, enteral or parenteral routes, by local topical application to the skin and the mucosa, or by injection, for example by subcutaneous injection. The medicines may also be given orally, for example in the form of tablets, coated tablets, film-coated forms, granules, capsules, soft capsules, solutions, syrups, emulsions, suspensions or aerosol mixtures. As stated above, depending on the form required, it will be best to use the product in the form of an aqueous-alcoholic solution or as a dry form. Administration is also possible by the rectal route, for example, in the form of suppositories, or by the parenteral route, for example in the form of injectable solutions or infusions, microcapsules or implants, by the percutaneous route, for example, in the form of ointment, solutions, pigments or colourings, by the transdermal route (patches) or by other routes such as those involving aerosols or nasal sprays.

These pharmaceutical compositions are prepared by conventional methods, in which pharmaceutically inert, organic or inorganic excipients are added to the compositions obtained according to the invention. These compositions may therefore be solids or liquids, presented in any of the pharmaceutical forms commonly used in human medicine, as for example plain or sugar-coated tablets, pills, lozenges, capsules, drops, granules, injectable preparations, ointments, creams or gels, prepared by standard methods. For the production of plain or sugar-coated tablets, coated tablets and hard gelatine capsules it is possible to use, for example, lactose, corn starch or derivatives thereof, talcum and stearic acid or its salts.

Suitable carriers for soft gelatine capsules or for suppositories comprise for example, fats, waxes, semi-solid or liquid polyols, natural or modified oils, etc. Suitable vehicles for the preparation of solutions, for example, injectable solutions, emulsions or syrups, comprise, for example, water, alcohols, glycerol, polyols, sucrose, invert sugars, glucose, vegetable oils, etc. Suitable carriers for microcapsules or implants comprise, for example, copolymers of glyoxalic acid and lactic acid. The active ingredients as defined above may be blended with the excipients usually employed in pharmaceutical compositions, such as talcum, gum arabic, lactose, starch, magnesium stearate, cocoa butter, aqueous or non-aqueous vehicles, fatty substances of animal or vegetable origin, paraffin derivatives, glycols, various wetting agents, dispersants or emulsifiers and preservatives. In addition to the active ingredients as defined above and the excipients, pharmaceutical compositions may contain additives such as, for example, diluents, disintegrators, binders, lubricants, wetting agents, stabilisers, emulsifiers, preservatives, sweeteners, colorants, flavours or fragrances, thickeners and buffering agents, and also solvents or solubilisers, retarders, osmotic pressure-modifying salts, coating materials or antioxidants. This invention also includes pharmaceutical compositions containing at least one of the drugs defined above as active ingredient.

When using the compositions obtained according to the invention, doses may vary within relatively wide limits and must be set according to the person being treated and the condition concerned. Pharmaceutical compositions normally contain from 0.2 to 500 mg, preferably from 1 to 200 mg, of active ingredients as defined above, in the form of dry extract. For oral administration, the daily dose generally varies between 0.05 and 10 mg/kg, preferably from 0.1 to 8 mg/kg, particularly from 0.1 to 6 mg/kg. For example, a daily dose varying from 5 to 500 mg would be appropriate for an adult. For intravenous administration, the daily dose varies approximately from 0.05 to 6 mg/kg, preferably from 0.1 to 5 mg/kg. The daily dose may be divided, especially when a large amount of active ingredient is to be administered.

DETAILED DESCRIPTION

Some examples will now be given below so as to illustrate the implementation of the invention in a non-restrictive manner. In view of the nature of the products, a fragrance or perfume should obviously be added when they are to be used in liquid or solid form.

EXAMPLES

Example 1

A composition was prepared containing:

| | |
|---|---|
| an aqueous-alcoholic extract of *Allium cepa*: | 87.04% |
| an aqueous-alcoholic extract of *Citrus lemon*: | 11.96% |
| an atomised aqueous-alcoholic extract of *Paullinia cupana*: | 0.50% |
| an atomised aqueous-alcoholic extract of *Theobroma cacao*: | 0.50% |

The aqueous-alcoholic extract of *Allium cepa* was prepared by picking, cleaning and milling the *Allium*, macerating in 96° alcohol for 48 hours in the cold, filtering through a 0.22-micron filter, collecting the alcoholic filtrate and adjusting to 30° alcohol.

The aqueous-alcoholic extract of *Citrus lemon* was prepared by picking, cleaning and milling the *Citrus*, macerating in 96° alcohol for 48 hours in the cold, filtering through a 0.22-micron filter, collecting the alcoholic filtrate and adjusting to 30° alcohol.

A master solution containing the aqueous-alcoholic extracts of *Allium* and *Citrus* was prepared by simple mixing, then the atomised aqueous-alcoholic extracts of *Paullinia cupana* and *Theobroma cacao* were added to this master solution to give the required combined extract.

Example 2

A composition was prepared containing:

| | |
|---|---|
| an aqueous-alcoholic extract of *Allium cepa*: | 87.30% |
| an aqueous-alcoholic extract of *Citrus lemon*: | 12.00% |
| an atomised aqueous extract of *Salix alba*: | 0.50% |
| zinc sulphate hexahydrate: | 0.20% |

The aqueous-alcoholic extract of *Allium cepa* was prepared by picking, cleaning and milling the *Allium*, macerating in 96° alcohol for 48 hours in the cold, filtering through a 0.22-micron filter, collecting the alcoholic filtrate and adjusting to 30° alcohol.

The aqueous-alcoholic extract of *Citrus lemon* was prepared by picking, cleaning and milling the *Citrus*, macerating in 96° alcohol for 48 hours in the cold, filtering through a 0.22-micron filter, collecting the alcoholic filtrate and adjusting to 30° alcohol.

A master solution containing the aqueous-alcoholic extracts of *Allium* and *Citrus* was prepared by simple mixing, then the aqueous extract of *Salix alba* and the zinc sulphate hexahydrate were added to this master solution to give the required combined extract.

Example 3

A food supplement was prepared containing:

| | |
|---|---|
| a dry extract of *Allium cepa*: | 87.04% |
| a dry extract of *Citrus lemon*: | 11.96% |
| a dry extract of *Paullinia cupana*: | 0.50% |
| a dry extract of *Theobroma cacao*: | 0.50% |

This was obtained by adding an aroma to the composition obtained in Example 1 and then freeze-drying the mixture to give a powder which could be used directly as a food supplement.

Example 4

A cosmetic lotion for scalp treatment was prepared from the following components:

| | |
|---|---|
| composition obtained in Example 1 | 21 ml |
| excipient qsp (including perfume/aroma) | 100 ml |

The lotion was prepared by simple mixing of the composition obtained in Example 1 and an excipient.

Example 5

A medicinal lotion for scalp treatment was prepared from the following components

| | |
|---|---|
| composition obtained in Example 2 | 40 ml |
| excipient qsp (including perfume/aroma) | 100 ml |

The lotion was prepared by simple mixing of the composition obtained in Example 2 and an excipient.

Example 6

Tablets with the following formulation were prepared:

| | |
|---|---|
| composition obtained in Example 3 | 100 mg |
| excipient qsp (including perfume/aroma) | 300 mg |

(excipient details: lactose, talcum, starch, magnesium stearate)

Example 7

An ointment for medicinal use was prepared as follows:

| | |
|---|---|
| composition obtained in Example 3 | 5 ml |
| excipient qsp (including perfume/aroma) | 100 gl. |

1) Study of Anti-Hair Loss Effectiveness Using the Phototrichogram Method with Hair Treatment Used Under Normal Conditions of Use During 12 consecutive weeks 20 male volunteers, aged from 35-55 and having slight to moderate baldness corresponding to types II-IV of the Hamilton scale were treated using the composition of example 4 (Hamilton scale: type 1: slightly receding hairline, type II: receding hairline at the temples and thinning of the region of the vertex, type III: meeting of the temporal recession and the vertex bald spot, type IV: baldness except for region of the temples, type V hair loss in the vertex).

The protocol was the following:

Day 1: location of the temporal site, cross-sections of hair at the point of emergence from the scalp, macrophotography of the region studied, Days 1-2: no application of product, no shampooing, Day 3: new macrophotography of the same region as at day 1 and beginning of treatment:

Days 3-42: application of the product to the scalp twice a day (2-3 sprays on each occasion), Day 42: evaluation of capillary and skin tolerance, location of the temporal site, cross sectioning of the hair at the point of emergence from the scalp, macrophotography of the region studied, Days 42-43: no application of product and no shampooing, Day 44: fresh macrophotography of the same region as at day 1, Days 44-84 application of the product understudy to the scalp twice a day (2-3 sprays on each occasion), to the site of cross-section of the hair at the point of emergence from the scalp, Day 84: evaluation of capillary and skin tolerance, location of the temporal site of the region studied, cross sectioning of the hair at the point of emergence from the scalp, macrophotography of the region studied, Days 84-85: no application of the product and no shampooing, Day 86: new macrophotography of the same region as at day 1.

The study showed:
- a significant anti-hairloss effectiveness after six weeks of treatment: statistically significant increase in the A/T ratio (anagenic/telogenic ratio) of +44.91%
- significant anti-hairloss effectiveness after 12 weeks of treatment: statistically significant increase in the NT ratio (anagenic/telogenic ratio) of +46.78%
- good clinical tolerance: no skin reaction was observed during dermatological examination
- good subjective clinical tolerance: one volunteer did nevertheless describe experiencing cutaneous discomfort.

2) Evaluation of Angeogenesis Activity of the Compounds of Examples 1 and 2

The product of the invention was tested on Angiokit plates. Using well-known tests, the development of endothelial cells in co-culture with fibroblasts was checked, and the formation of capillary structures (tubules) was observed. The product tested at differing concentrations was introduced onto each plate into certain wells. Certain wells additionally received an activator (VEGF) while other wells received an inhibitor (Suramine). Some wells acted as controls.

The nutrient medium was changed at days 3, 4, 7, 10 and 12 and the test was terminated at day 15.

The results observed on day 15 showed that the product has pronounced angiogenic activity.

The invention claimed is:

1. A composition comprising: from 65% to 93% of an aqueous-alcoholic extract of *Allium* species; from 5% to 33% of an aqueous-alcoholic extract of *Citrus* species; from 0.25% to 2.5% of an aqueous-alcoholic extract of *Paullinia* species; and from 0.25% to 2.5% of an aqueous-alcoholic extract of *Theobroma* species.

2. The composition according to claim 1, wherein the *Allium* species is *Allium cepa*, the *Citrus* species is *Citrus lemon*, the *Paullinia* species is *Paullinia cupana*, and the *Theobroma* species is *Theobroma cacao*.

3. The composition according to claim 2, comprising approximately 87% of the aqueous-alcoholic extract of *Allium cepa*, approximately 12% of the aqueous-alcoholic extract of *Citrus lemon*, approximately 0.5% of an atomized aqueous-alcoholic extract of *Paullinia cupana* and approximately 0.5% of an atomized aqueous-alcoholic extract of *Theobroma cacao*.

4. A medicine containing the composition according to claim 1, wherein the medicine stimulates and encourages the regrowth of hair.

5. A method for the preparation of the composition according to claim 1 comprising:
preparing an aqueous-alcoholic extract of *Allium* species, an aqueous-alcoholic extract of *Citrus* species; an aqueous-alcoholic extract of *Paullinia* species; and an aqueous-alcoholic extract of *Theobroma* species;
combining the aqueous-alcoholic extract of *Allium* species and the aqueous-alcoholic extract of *Citrus* species to form a first solution;
mixing the first solution with the aqueous-alcoholic extract of *Paullinia* species; and the aqueous-alcoholic extract of *Theobroma* species to obtain the composition.

6. The method of preparation according to claim 5, further comprising preparing the first solution by picking, cleaning, milling and macerating the *Allium* species and the *Citrus* species for several hours in an aqueous-alcohol, filtering the mixture to form an aqueous extract, adjusting the aqueous-alcoholic extract and mixing with the other ingredients.

7. A method for treating the hair and/or scalp of a subject comprising administering to the hair and/or scalp of the subject the composition according to claim 1, wherein the treatment provides for at least one of:
slowing down the loss of hair;
stimulating hair growth;
increasing the density of hair; and
treating the signs of ageing scalp.

* * * * *